US010105072B2

(12) United States Patent
Chetelat et al.

(10) Patent No.: US 10,105,072 B2
(45) Date of Patent: Oct. 23, 2018

(54) MEASUREMENT DEVICE FOR MEASURING BIO-IMPEDANCE AND/OR A BIO-POTENTIAL OF A HUMAN OR ANIMAL BODY

(71) Applicant: CSEM CENTRE SUISSE D'ELECTRONIQUE ET DE MICROTECHNIQUE SA—RECHERCHE ET DÉVELOPPEMENT, Neuchatel (CH)

(72) Inventors: Olivier Chetelat, Cudrefin (CH); Marc Correvon, Cornaux (CH)

(73) Assignee: CSEM CENTRE SUISSE D'ELECTRONIQUE ET DE MICROTECHNIQUE SA—RECHERCHE ET DÉVELOPPEMENT, Neuchatel (CH)

( * ) Notice: Subject to any disclaimer, the term of this patent is extended or adjusted under 35 U.S.C. 154(b) by 791 days.

(21) Appl. No.: 14/576,925

(22) Filed: Dec. 19, 2014

(65) Prior Publication Data

US 2015/0173677 A1    Jun. 25, 2015

(30) Foreign Application Priority Data

Dec. 20, 2013   (EP) .................................... 13198776

(51) Int. Cl.
*A61B 5/04*       (2006.01)
*A61B 5/0408*    (2006.01)
(Continued)

(52) U.S. Cl.
CPC ........ *A61B 5/04085* (2013.01); *A61B 5/0428* (2013.01); *A61B 5/053* (2013.01); *A61B 5/6805* (2013.01)

(58) Field of Classification Search
CPC ... A61B 5/04085; A61B 5/0428; A61B 5/053; A61B 5/6805
See application file for complete search history.

(56) References Cited

U.S. PATENT DOCUMENTS

| 6,434,420 | B1* | 8/2002 | Taheri | ................. | A61B 5/0408 |
| | | | | | 600/372 |
| 2011/0001497 | A1 | 1/2011 | Chetelat et al. | | |
| 2012/0215076 | A1* | 8/2012 | Yang | .................... | A61B 5/0205 |
| | | | | | 600/301 |

FOREIGN PATENT DOCUMENTS

| EP | 2394571 | 12/2011 |
| EP | 2567657 | 3/2013 |
| WO | 01/54563 | 8/2001 |

OTHER PUBLICATIONS

European Search Report for EP13198776 dated May 26, 2014.

* cited by examiner

*Primary Examiner* — Amanda Hulbert
(74) *Attorney, Agent, or Firm* — Pearne & Gordon LLP (57) ABSTRACT

Measurement device for measuring a bio-impedance and/or a bio-potential of a human or animal body and adapted to be worn on the body, including: at least two electrode sensors. Each of the at least two electrode sensors includes a first electrical contact configured to be in electrical contact with the skin of the body when the system is worn, and a second electrical contact. A single electrical connector electrically connects the at least two electrode sensors with each other via the second electrical contact. An active device is configured to cooperate with a subset of the at least two electrode sensors such that the potential of the electrical connector is substantially equal to a projected potential (Continued)

determined from the potential of the first electrical contact of each electrode sensor of the subset when the measurement device is worn.

21 Claims, 8 Drawing Sheets

(51) Int. Cl.
*A61B 5/0428* (2006.01)
*A61B 5/053* (2006.01)
*A61B 5/00* (2006.01)

MEASUREMENT DEVICE FOR MEASURING BIO-IMPEDANCE AND/OR A BIO-POTENTIAL OF A HUMAN OR ANIMAL BODY

FIELD

The present invention concerns a measurement device adapted to be worn on the body of a human or animal for measuring a bio-impedance and/or a bio-potential of the body.

DESCRIPTION OF RELATED ART

The most used method to measure biopotentials (e.g., ECG, EEG, EMG, EOG, etc.) is to use electrodes made of a conductive material in contact with the skin. Each electrode is electrically connected to a centralized electronic unit amplifying and acquiring the potential signals. The cables are insulated and preferably shielded. They connect the electrodes with the centralized electronic unit in a star arrangement, where the centralized electronic unit is the common point to which all cables converge. The electrode can be made of a piece of $Ag/Ag^+Cl^-$ interfaced to the skin with a gel. Such electrodes are most of the time disposable and passive. Other types of electrodes include conductive material (metal, conductive rubber/silicone, conductive textile, conductive tape, etc.) in direct contact with the skin (dry electrodes), or interfaced to the skin with gel or liquid (water, saline, sweat, etc.). The electrodes may also physically perforate the skin to get a direct contact with the moisturized tissues under the dry upper layers of the skin.

The measurement of bioimpedance or the electrical stimulation of a body part is performed the same way as the measurement of biopotentials, except that current is injected, at least at some electrodes.

The method presented so far has the drawback to require cables, which let the subject resemble to a "Christmas tree" in the sense that the overall integration is poor. Another method that somewhat alleviates this problem affixes on the body adhesive patches or bandages comprising two or more electrodes and sometime also including a miniaturized centralized electronic unit. In this case, the cables connecting the electrodes to the centralized electronic unit are no longer apparent, but embedded in the patch.

Another similar method allowing concealing the cables is to embed them in a garment. They can even be made of conductive textile in some situations. In this approach, the electrodes are also part of the garment, which makes the donning and doffing as easy as to put on or take off a normal garment.

Typical known products include a Holter's ECG recorder, where an insulated and shielded cable has to connect each electrode to the centralized electronic unit that amplifies and acquires the data. This results in a poor overall integration. In addition to the patient discomfort, such approach may suffer from accidental pulling of cable, which would make signal artifact if not totally interrupt the monitoring of the signals. All cables are connected to the centralized electronic unit in a star arrangement with the electronic unit being the convergence center.

CaridioInsight's product allows measuring 250 ECG leads with electrodes embedded in a patch. In this product, the connection still follows the same topology as the one of the Holter's recorder (centralized electronic unit not shown in the picture). A star arrangement with 250 connections makes the integration very difficult.

Telzuit proposes a patch integrating the electrodes, the cables, and the centralized electronic unit. The topology is still the same as the one of the Holter's recorder, namely a star arrangement with the center in the centralized acquisition electronics.

Weartech's smart shirt integrates textile electrodes. The electrical connections are made of conductive textile. They are not particularly shielded or insulated in this product, but this may degrade the signal quality especially in the presence of sweat or electromagnetic disturbances. The effect of these drawbacks is limited to an acceptable level in the targeted application (sports) by keeping the electrodes close to the centralized electronic unit.

Camtech product consists of two electrodes. The centralized electronic unit is located on top of one of the electrodes. The system is limited to two electrodes. However, if it were extended to more electrodes, the connection would still be a start arrangement with all cables converging to the centralized electronic unit. Moreover, the cable is conventional, i.e., insulated and shielded.

In a product commercialized by SenseCore, the electrodes are standalone electrode sensors or more generally sensing and stimulating standalone electrode sensors. The product is made of only two electrode sensors (one reference standalone electrode sensor and one measuring/injecting standalone electrode sensor). However, the product could be extended to more measuring/injecting standalone electrode sensors. In this case, the electrodes would be connected to the same electrical connection in any chosen arrangement, i.e., not limited to a star arrangement with its center at a specific point. Moreover, the electrical connection does no longer need to be shielded or insulated and can easily be made of conductive fabrics. Therefore, such system is usually made of a garment electrically connecting the sensors.

Patent applications US20110001497 and EP2567657 by the present applicant disclose systems that require electrode sensors to have two contacts with the body. Such electrode sensors are named "bi-contact electrode sensors". They allow making systems that measure biopotentials with outstanding signal quality in the presence of electromagnetic disturbances. Moreover, thanks to the two contacts of the reference electrode sensor, the potential of the electrical connection (conductive garment) is close to the one inside the body. This allows the electrical connection to be not insulated. Bi-contact electrode sensors also allow measuring bioimpedance with only one electrical connection between the sensors, while being insensitive to the skin impedance as with the four-wire method which is the classical approach to measure bioimpedance. The four-wire method separates the injected current from the measurement of the resulting voltage by using two different sets of electrodes. In contrast with the approach disclosed in US20110001497 and EP2567657, the four-wire method cannot connect all electrode sensors with only one electrical connection.

A first limitation of the bi-contact approach disclosed in US20110001497 and EP2567657 when used with a single electrical connection is the sensitivity of its impedance variations which may be caused by varying tensions on the garment during motion, for instance.

A single electrical connection is much easier to obtain than multiple ones. One reason is because it relaxes the insulation requirements between electrical connections. Another one is because the connecting of the electrical connection with the sensors is simpler. Finally, the manufacture is cheaper. However, as disclosed in EP2567657, two electrical connections can solve the problem of sensitivity to impedance variations and allow one to recharge all electrode sensors while they remain in the garment. No solution has been proposed in the prior art to do the same with only a single electrical connection.

Another difficulty when using bi-contact electrode sensors comes from the distance between their two contacts that cannot be too small. Too-close contacts can result to the loss of the bi-contact effect. In such case, the two contacts behave like if they were short-circuited. Therefore, the size of the bi-contact electrode sensors cannot be reduced beyond a certain limit due to the minimum distance between the two contacts.

Furthermore, the manufacture of bi-contact electrode sensors is relatively costly and difficult, especially to obtain hermetic sensors (desired due to the presence of moisture or sweat, or if one wants the sensors to be used by swimmers/divers or to be washable with the garment in the washing machine). The necessity to alternate conductive materials (for the two contacts) with insulated material (between them) and possibly some sealing material also increases the risk to develop skin sensitivity (e.g., allergy) to one of the used materials.

SUMMARY

The present disclosure concerns a measurement device for measuring a bio-impedance and/or bio-potentials of a human or animal body and adapted to be worn on the body, comprising at least two electrode sensors; each of said at least two electrode sensors comprising a first electrical contact configured to be in contact with the skin of the body when the system is worn, and a second electrical contact; and a single electrical connector electrically connecting said at least two electrode sensors with each other via the second electrical contact; wherein an active device configured to cooperate with a subset of said at least two electrode sensors such that the potential of the electrical connector is substantially equal to a projected potential determined from the potential of the first electrical contact of each electrode sensor of said subset, when the measurement apparatus is worn.

An advantage of the measurement device disclosed herein is that the electrical connector is at a potential close to the one in the user's body, despite any mains disturbance or any current injected by the measuring sensor electrodes. Thus, no current flows from the electrical connector into the user's body by capacitive coupling or even by direct contact in the case the electrical connector is not insulated from the skin. As a matter of fact, the high impedance of the skin becomes in this case an ally because it insulates the electrical connector from the user's body inside. Therefore, a garment on which the measuring device is attached when worn by the user can be simply made of conductive fabrics without the necessity to provide any particular insulation.

Another advantage is that the measured bio-potentials are smaller and can more easily be within the input range of the electronic amplifiers. Moreover, inaccuracies of the amplifier gains or of the sample times have much less impact when the electrical connector is at a potential close to the one in the user's body. The electrical connector does not need to be shielded, nor insulated. One such single electrical connector is easy to manufacture. Sensitivity to impedance variations of electrical connection of garment can be drastically limited thanks to a connection method. Simultaneous recharging of bipolar electrode sensors is simple.

BRIEF DESCRIPTION OF THE DRAWINGS

The invention will be better understood with the aid of the description of an embodiment given by way of example and illustrated by the figures, in which.

DETAILED DESCRIPTION OF POSSIBLE EMBODIMENTS OF THE INVENTION

Figure 2:
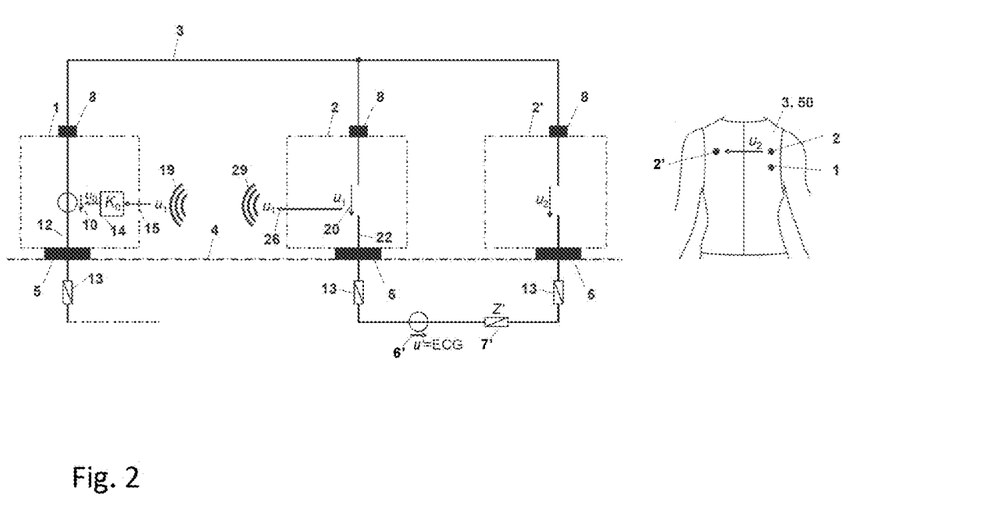
FIG. 2 illustrates the measuring device comprising a communication device for transmitting a voltage measured at the measuring electrode sensor and a controller comprised in the reference electrode sensor, according to an embodiment.

FIG. 2 illustrate a measurement device for measuring a bio-potential of a human or animal body and destined to be worn on the body, according to an embodiment. The measurement device comprises a reference electrode sensor 1, a first measuring electrode sensor 2, and a second measuring electrode sensor 2'. Each of the electrode sensors 1, 2, 2' comprises a first electrical contact 5 destined to be in electrical contact with the skin of the body when the measurement device is worn on the body, and a second electrical contact 8. The measurement device further comprises a single electrical connector 3 electrically connecting the electrode sensors 1, 2, 2' with each other via the second electrical contact 8.

The reference electrode sensor 1 comprises a voltage source 10 controllable by a controller 14. The first measuring electrode sensor 2 comprises a voltage measuring device 20. The voltage measuring device 20 is configured for measuring a voltage u1 between the first and second electrical contacts 5, 8 of the first measuring electrode sensor 2 when the measurement apparatus is worn.

The measured voltage u1 can be inputted to the controller 14 controlling the voltage source 10 such that the voltage u1 between the first and second electrical contacts 5, 8 of the first measuring electrode sensor 2 is set to zero. The first measuring electrode sensor 2 has a substantially infinite impedance between the first and second electrical contacts 5, 8 (for a predetermined frequency band). In this configuration, the potential of the electrical connector 3 is substantially equal to the potential of the first electrical contact 5 of the first measuring electrode sensor 2, and thus to the potential (bio-potential 6) inside the body when the measurement device is worn.

The measurement device comprises transmission means for transmitting the measured voltage u1 (signal 26 in FIG. 2) from the voltage measuring device 20 to an input 15 of the controller 14 that controls the voltage source 10. In the embodiment of FIG. 2, the transmission means comprises a wireless device 19, 29.

The second measuring electrode sensor 2' can also comprise a voltage measuring device 20 such that a bio-potential 6 of the body can be determined by measuring a voltage u2 between the first and second electrical contacts 5, 8 of the second measuring electrode sensor 2', when the voltage u1 is set to zero and when the measurement apparatus is worn. The second measuring electrode sensor 2' can have a current source 21 set to zero current and thus corresponding to an open circuit. In FIG. 2, bio-potential is represented by a voltage source 6 and the skin impedance by the two impedances 13.

Figure 3:
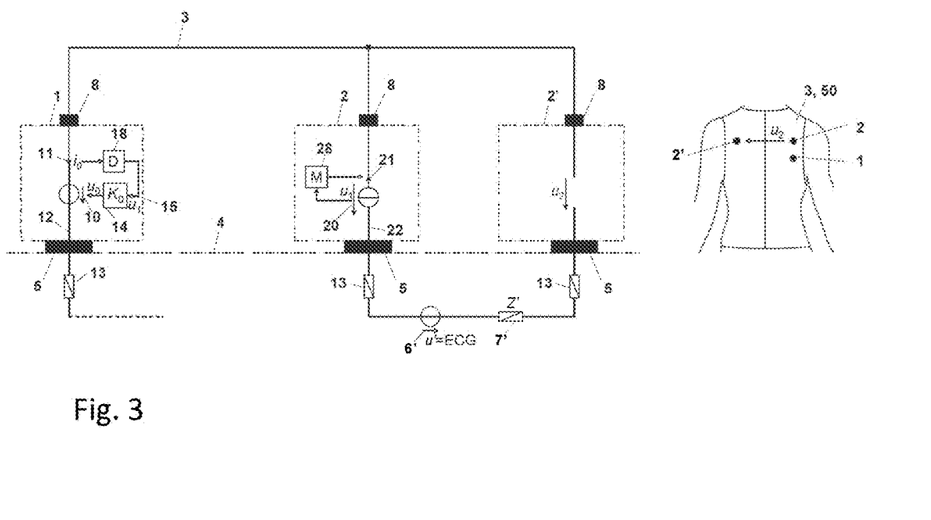
FIG. 3 represents the measuring device of FIG. 2 comprising the communication device, according to an embodiment.

In another embodiment illustrated in FIG. 3, the transmission means comprises means for encoding the voltage u1 using a high communication frequency band, for example of 2 MHz, on the electrical connector 3, and for decoding the encoded measured voltage u1. The voltage u1 can be encoded in bits (digital encoding) as in any modern communication line. If the encoding is analogue, the controller can also be analogue and would typically be of the form −g/s, where s is the Laplace variable and g the gain of the integrator. In the particular example of FIG. 3, the transmission means comprises a modulator 28 for modulating the measured voltage u1. The modulated voltage u1 can be demodulated in a demodulator 18 such that the modulated voltage u1 can be inputted in the input 15. Modulating the voltage u1 can be performed using a high frequency carrier such as a current generated at 2 MHz by a current source 21 comprised in the first measuring electrode sensor 2, using the modulator 28. The modulated current is then demodulated by the demodulator 18. The demodulator 18 can be a rectifier followed by a low-pass filter.

The measuring device can comprise a plurality of reference electrode sensors 1, and a plurality of measuring electrode sensors 2, 2'; each electrode sensors 1, 2, 2' comprising the first and second electrical contacts 5, 8 and being electrically connected with each other with the electrical connector 3 via the second electrical contact 8. The voltage source 10 can be comprised in one or more reference electrode sensors 1. In such case, the voltage source 10 of each of the plurality of reference electrode sensors 1 can be set to the same value. Alternatively, the voltage source 10 of each of the plurality of reference electrode sensors 1 can comprise weighed values, for instance, the voltage source 10 of one of the plurality of reference electrode sensors 1 can be driven with a voltage X times the one of the other reference electrode sensors 1.

The voltage measuring device 20 can be comprised in a subset of the plurality of measuring electrode sensors 2, 2', such that a plurality of voltages u1 can be measured from each measuring electrode sensor 2, 2' of the subset. In such configuration, the plurality of voltages u1 can be inputted to the controller 14 controlling the voltage source 10 for setting the potential of the electrical connector 3 substantially equal to a projected potential determined from the potential of the first electrical contact 5 of each electrode sensor 2, 2' of the subset.

The projected potential can comprise the average of the plurality of the potentials of the first electrical contact 5 of each electrode sensor 2, 2' of the subset. Alternatively, the projected potential can comprise a maximum, a minimum, or a median of the plurality of the potentials.

In a variant, the subset of the plurality of measuring electrode sensors 2, 2' comprises all of the measuring electrode sensors 2, 2'.

The bio-potential 6 of the body can be determined by measuring the voltage u2 between the first and second electrical contacts 5, 8 of the plurality of measuring electrode sensors 2, 2' comprising the voltage measuring device 20 and not used for measuring the voltage u1. The measuring electrode sensors 2, 2' used for measuring the voltage u2 can have a current source 21 set to zero current and thus corresponding to an open circuit.

Figure 1:
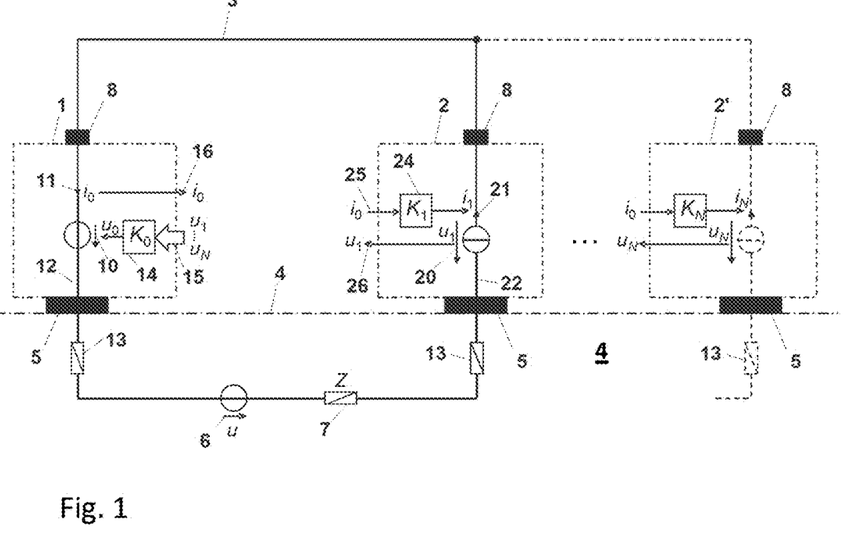
FIG. 1 represents a measuring device comprising at least one reference electrode sensor and at least two measuring electrode sensors, according to an embodiment.

FIG. 1 illustrates a generalization of the measuring device of FIG. 2 showing that the measuring device can comprise a plurality of the measuring electrode sensors controller 24 and current source 21 can be comprised in any one of the measuring sensor electrodes 2, 2'.

Figure 4:
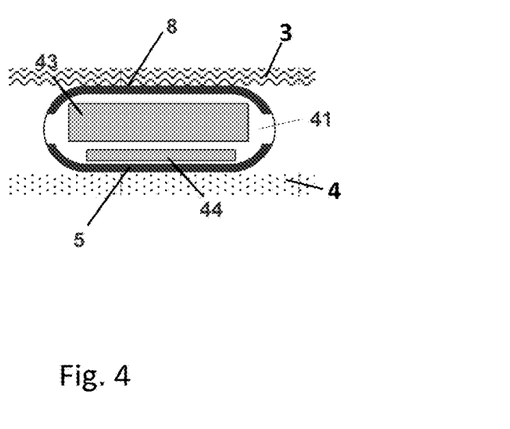
FIG. 4 shows a detailed view an electrode sensor of the measuring device, according to an embodiment.

FIG. 4 is a detailed view of one of the electrode sensors 1, 2, 2' according to an embodiment. The first electrical contact 5 is represented in contact with the skin 4 and the second electrical contact 8 is represented electrically contacting the electrical connector 3. The first and second electrical contacts 5, 8 can electrically contact the body 4 and the electrical connector 3, respectively, by galvanic or capacitive coupling. The electrode sensor 1, 2, 2' can further comprise a power supply 43 (for example a battery) or an energy harvesting device and an electronic circuit 44 that can be for instance an integrated circuit. The electronic circuit 44 typically picks up a physiological signal, such as for instance ECG. The electronic circuit 44 can also stimulate the body, such as for instance injecting a current for performing an impedance measurement. The electronic circuit 44 also allows the reference and/or measuring sensor electrode 1, 2, 2' to be isochronously synchronized and/or communicate with each other, for example using electromagnetic waves (wireless communication). The electrode sensor 1, 2, 2' can further comprise an insulator 41 for insulating the first and second electrical contacts 5, 8 from the power supply 43 and the electronic circuit 44. The electrode sensor 1, 2, 2' having the power supply 43 and the electronic circuit 44 can be considered as a standalone electrode sensor. Since the electrode sensors 1, 2, 2' comprise the two electrical contacts 5, 8, the power supply 43 and the electronic circuit 44, the electrode sensors 1, 2, 2' function as standalone bipolar electrode sensors.

In a preferred embodiment, the measuring device is configured to be attached to a garment 50 so that when the garment is worn in the body, the first electrical contacts 5 are electrically contacting the skin 4. The garment can be electrically conductive such that, when the measuring device is attached to a garment 50, the second electrical contacts 8 electrically contact the garment 50, the latter having the role of the electrical connector 3. The garment can also comprise an electrically conductive portion in contact with the second electrical contacts 8 of the electrode sensors when the measuring device is attached to a garment 50.

Figure 5:
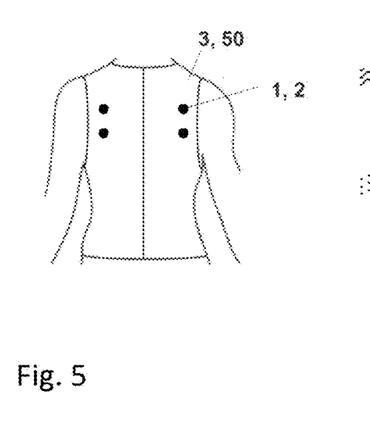
FIG. 5 represents a measuring device attached to an electrically conductive garment, according to an embodiment.

FIG. 5 represents the measuring device attached to an electrically conductive garment, wherein the measuring device comprises four electrode sensors, for example one reference electrode sensor 1 and three measuring electrode sensors 2.

Figure 6:
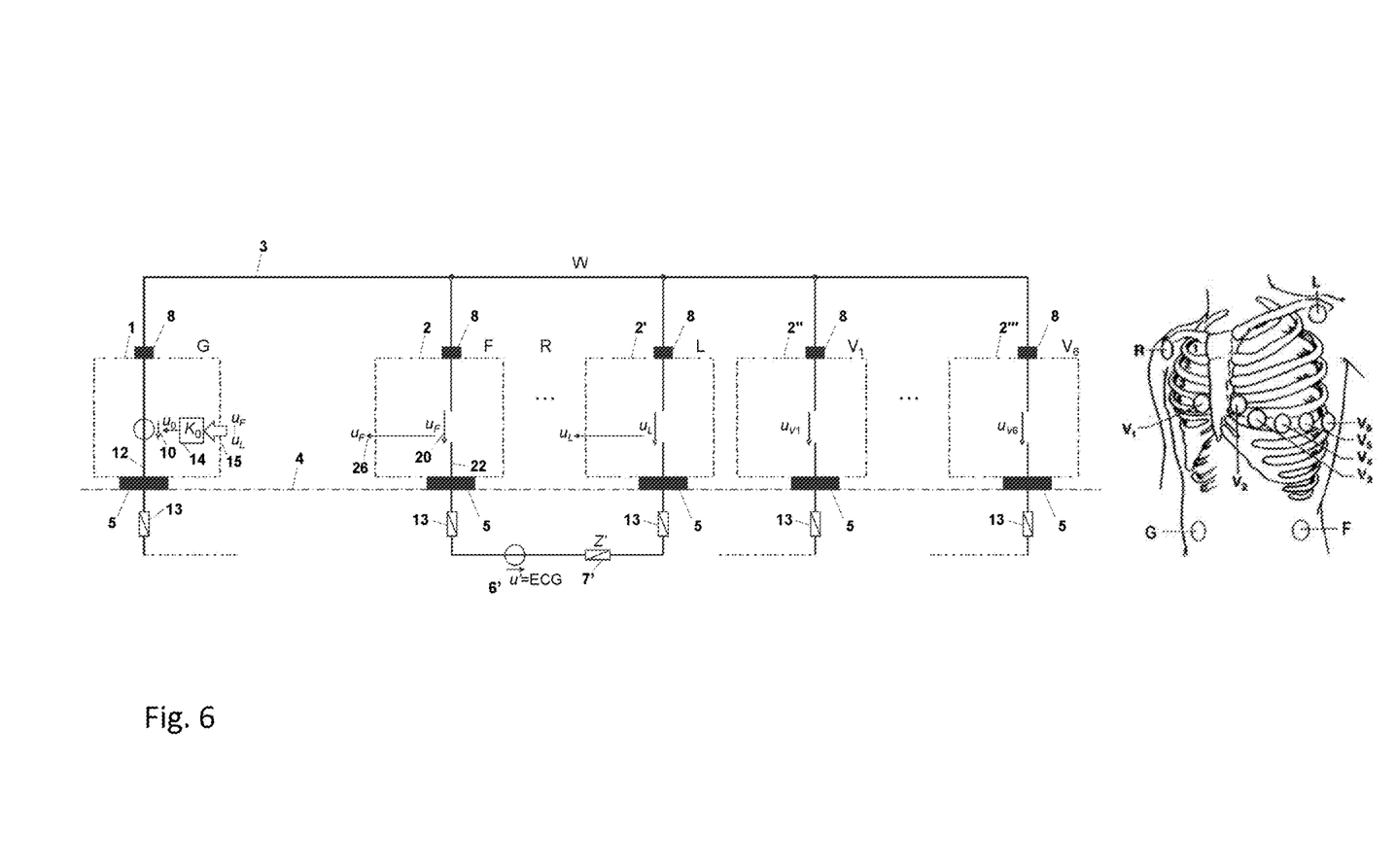
FIG. 6 represents the measuring device of FIG. 2 comprising a communication device (not explicitly shown), according to another embodiment.

In another embodiment represented in FIG. 6, the measuring device comprises one reference electrode sensor 1 comprising the voltage source 10 controllable with the controller 14, and nine measuring electrode sensors 2, 2', 2", 2'''. The voltage measuring device 20 is included in a subset of three of the nine measuring electrode sensors 2, 2' and is configured for measuring a voltage uF, uR, uL between the first and second electrical contacts 5, 8 for each of measuring electrode sensors 2, 2' of the subset, when the measurement device is worn. The measuring device of FIG. 6 corresponds to a 12-lead ECG measuring system wherein the reference electrode sensor 1 takes the place of the guard electrode G, the three measuring electrode sensors 2, 2' plays the role of electrodes F, R, and L, respectively. The six other measuring electrode sensors 2", 2''' correspond to precordial leads $V_1$ to $V_6$.

The voltages uF, uR, uL can be inputted to the controller 14 controlling the voltage source 10 such as to set the potential of the electrical connector 3 substantially equal to a projected potential determined from the potential of the first electrical contact 5 of each electrode sensor 2, 2' of the subset of the three measuring electrode sensors 2, 2'. Again, the projected potential can comprise the average, a maximum, a minimum, or a median of the plurality of the potentials of each electrode sensor 2, 2' of the subset. The potential of the electrical connector 3 thus corresponds to the Wilson's terminal of a 12-lead ECG measuring system. The six remaining precordial leads $V_1$ to $V_6$ can readily be measured by the measuring sensor electrodes 2", 2''' through their voltage $u_{vi}$. The voltages uF, uR, uL can be (signal 26) transmitted in real-time from each of the measuring electrode sensors 2, 2' of the subset to the controller input 1 wirelessly (via electromagnetic waves, such as Bluetooth or infrared), as described above.

Figure 7:
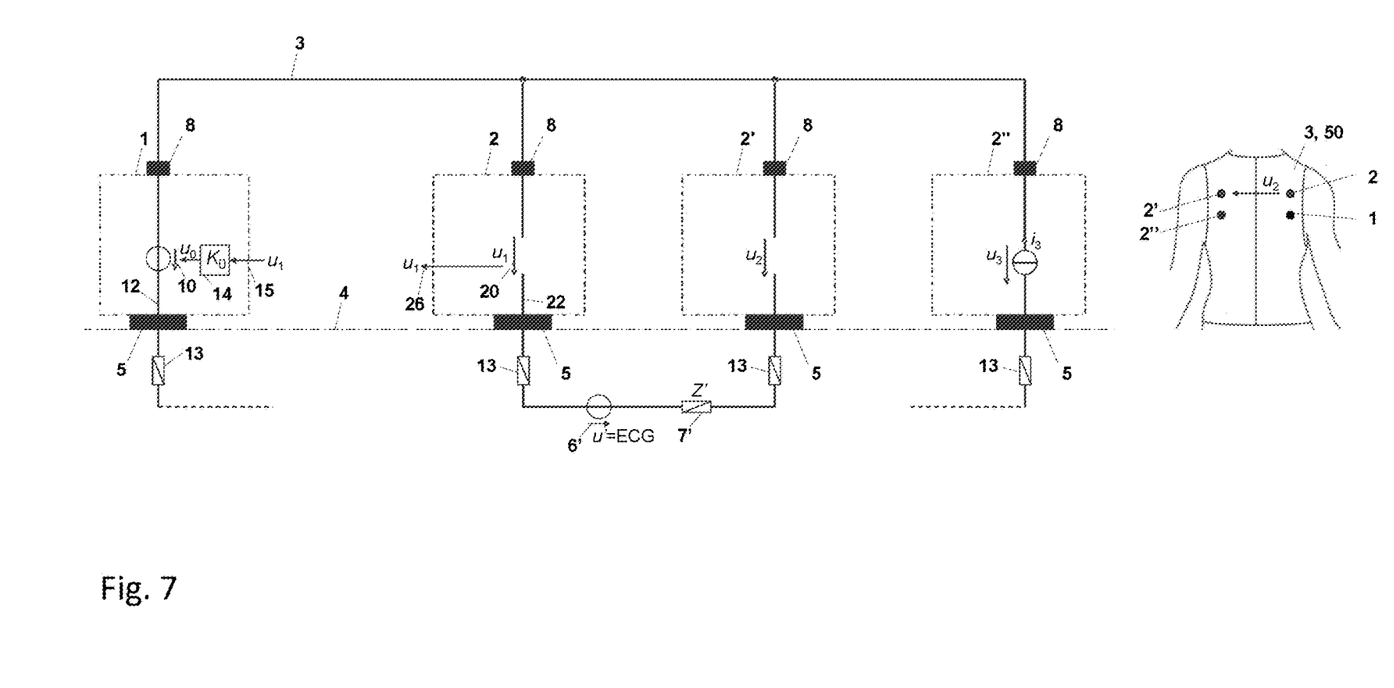
FIG. 7 represents the measuring device, according to yet another embodiment.

In another embodiment shown in FIG. 7, the measuring device further comprises a measuring electrode sensor 2" comprising a current source 21 configured for injecting an impedance current i3 passing in the reference electrode sensor 1. The measuring device of FIG. 7 allows for determining a bio-impedance 7 of the body as the quotient of the voltage u2 measured in the measuring electrode sensor 2', over the injected impedance current i3. During the measurement of the voltage u2, the voltage u1 is set to zero by the voltage source 10 as described above. The measuring electrode sensors 2' can comprise a current source 21 set to zero current (corresponding to an open circuit as shown in FIG. 7).

The impedance current i3 injected by the current source 21 of the measuring electrode sensor 2" can be used for electrical stimulation.

Alternatively, the impedance current i3 can be sunk (i.e., negatively injected) with another measuring electrode sensor 2, 2' using its current source 21 with the same but opposite current. In fact, any of the measuring electrode sensors 2, 2', 2" can inject or sink any desired current patterns. Moreover, several currents can be injected/sunk simultaneously on different channels, for instance at different frequencies or at different time slots. Finally, in order not to measure the skin impedance 13, it is preferable to use different electrode sensors for the current injection/sinking and for the voltage measurement.

Figure 8:
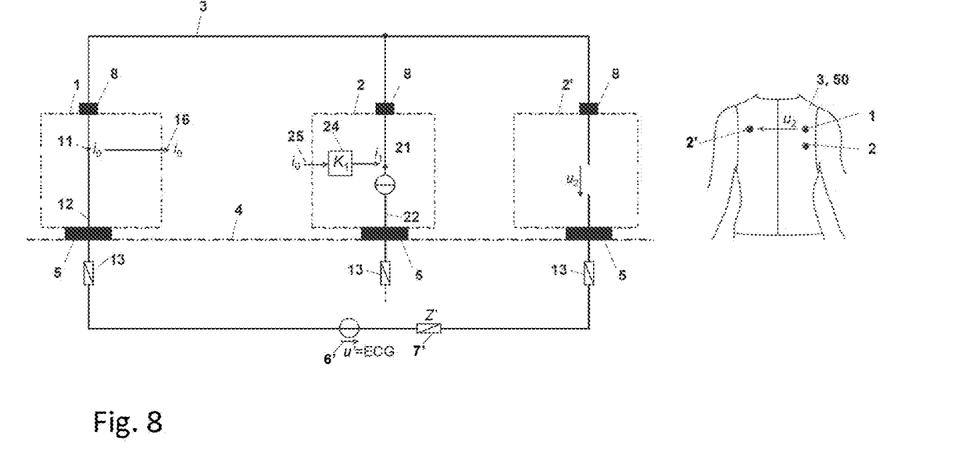
FIG. 8 represents the measuring device, according to yet another embodiment.

In yet another embodiment shown in FIG. 8, the measuring device further comprises a reference electrode sensor 1 and two measuring electrode sensors 2, 2'. One of the measuring electrode sensors 2 comprises a current source 21 controllable by a controller 24. The current source 21 is configured for injecting a current i1 in the reference electrode sensor 1 when the measurement device is worn. The current i1 can be inputted to the controller 24 such that the current source 21 sets the current i1 to zero. The potential of the electrical connector 3 is substantially equal to a projected potential determined from the potential of the first electrical contact 5 of each electrode sensor of the subset comprising the electrode sensor 1.

The bio-potential 6 of the body can be determined from the potential u2 measured at the other measuring sensor electrode 2' when the current i1 is set to zero.

The measuring device of FIG. 8 can further comprise a measuring electrode sensor comprising a current source (not shown in FIG. 8) configured for injecting an impedance current (also not shown) passing in the measuring electrode sensor 2 as a result of the feedback loop setting the current i1 to zero. The bio-impedance 7 of the body can be determined as the quotient of the voltage u2 measured in the measuring electrode sensor 2', over the injected impedance current. The impedance current injected by the current source 21 of the measuring electrode sensor 2" can also be used for electrical stimulation.

Figure 9:
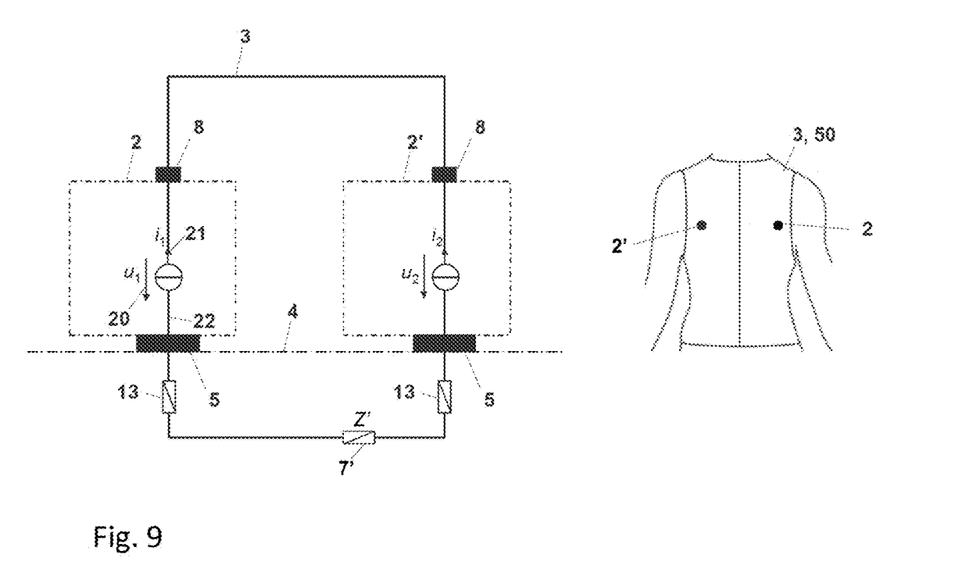
FIG. 9 represents the measuring device, according to yet another embodiment.

In yet another embodiment represented in FIG. 9, the measuring device comprises a measuring electrode sensor 2 and another measuring electrode sensor 2'. A first current i1 is injected by the current source 21 of the first measuring electrode sensor 2. A second current i2 is also injected using the current source 21 of the second measuring electrode sensor 2'. The second current i2 has substantially same magnitude than the first current i1 but has an opposed polarity. The potential of the electrical connector 3 is thus substantially equal to a projected potential determined from the potential of the first electrical contact 5 of each measuring electrode sensors 2, 2' when the measurement apparatus is worn.

In this configuration, the bio-impedance of the body can be determined by dividing the potential difference $u_1-u_2$ measured in the measuring electrode sensors 2 and 2' with the second current i2.

Figure 10:
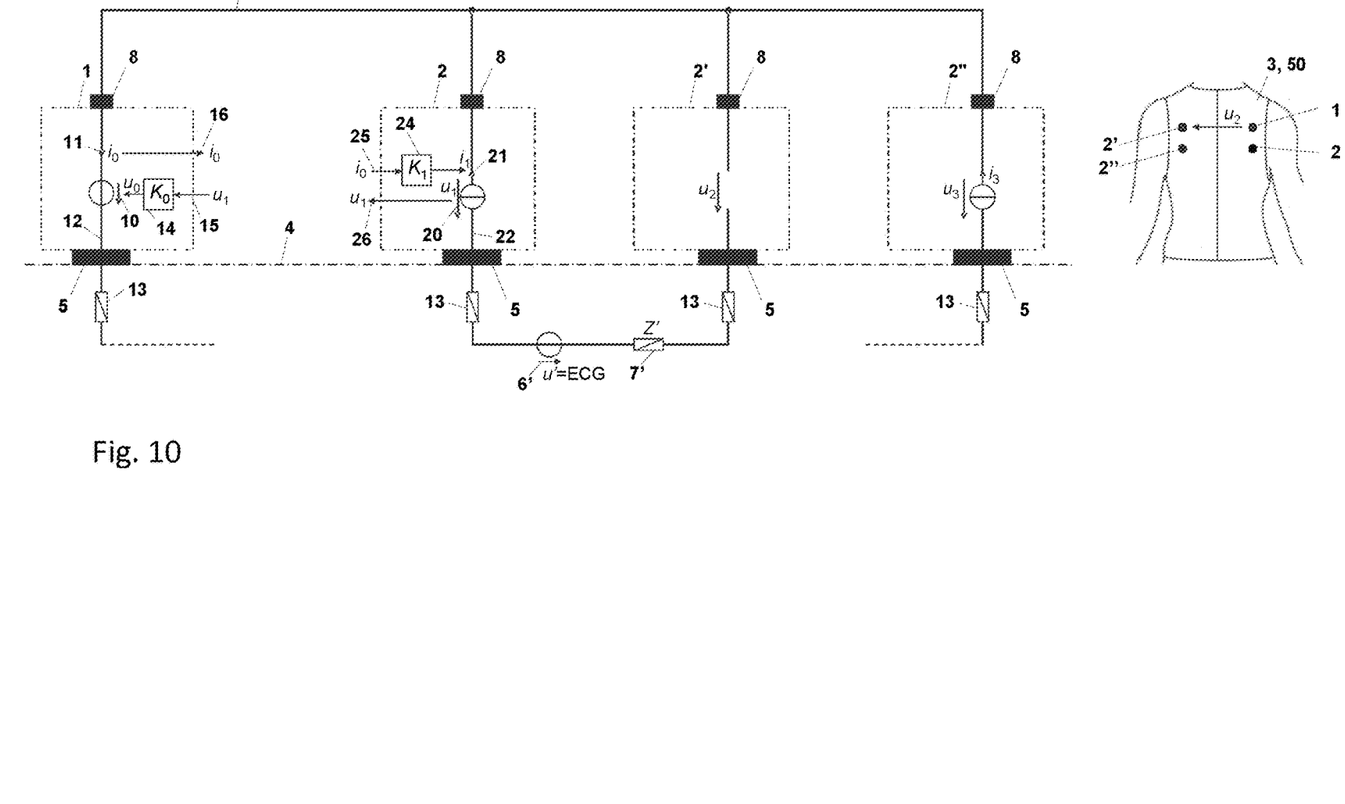
FIG. 10 represents the measuring device, according to yet another embodiment.

The different measurement devices described above can be combined. For instance, in an embodiment shown in FIG. 10, the bio-potential 6 (or ECG) can be measured using the method according to any of the embodiments of FIGS. 7 to 11 at a bio-potential frequency band comprised between about 1 to 1000 Hz. The bio-impedance can be measured using the method of FIG. 8 and the impedance current i3 being modulated in the impedance frequency band at about 50 kHz. Moreover, the transmission means can be arranged for transmitting the measured voltage u1 at a communication frequency band being typically above 1 MHz.

Figure 11:
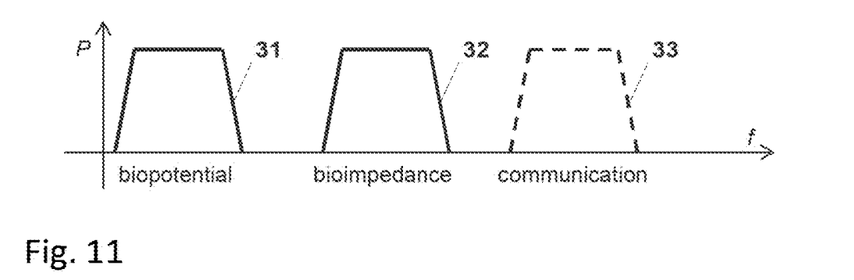
FIG. 11 shows frequency bands used in the measuring device, according to an embodiment.

FIG. 11 represents the different frequency bands including the bio-potential frequency band 31, the impedance frequency band 32 and the communication frequency band 33. The communication frequency band 33 corresponds to the current 21 generated at 2 MHz for transmitting the first voltage u1 (as explained in FIG. 3). The impedance band 32 can be divided in several sub-bands, one for each impedance channel. In this case, not all frequency bands (or channels) have to follow the same method: a different method can be chosen for some of them if desired.

The controllers 14, 24 comprised respectively in the reference sensor electrode 1 and the measurement electrode sensor 2 can have, for instance, their control law described by a transfer function equal to $-g/(1-z^{-1})$, where z is the variable of the z-transform and g the gain of the resulting integrator. The controller 14, 24 can be physically in any electrode sensor 1, 2, distributed on several electrode sensors 1, 2, or even outside the measurement device. However, the preferred location for the controller 14 is in the reference electrode sensor 1 where a microcontroller executes the control law.

The controllers 14, 24 can be single controllers as described above or two low-bandwidth controllers about a given frequency, one for the envelop of the cosine wave and one for the envelop of the sine wave (at the given frequency).

Figure 12:
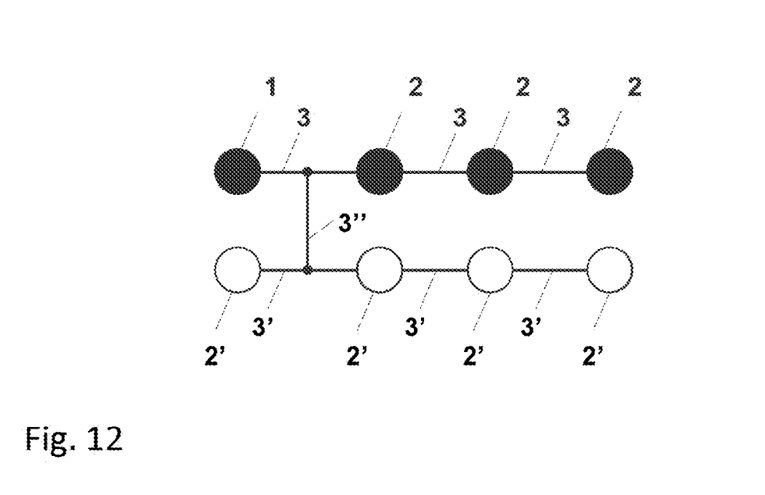
FIG. 12 illustrates an arrangement of a reference electrode sensor and measuring electrode sensors of the measuring device, according to an embodiment.

FIG. 12 illustrates a particular arrangement of the reference electrode sensor 1 and measuring electrode sensors 2 according to an embodiment. In the arrangement of FIG. 12, the electrical connector comprises a first branch 3 electrically connecting the reference electrode sensor 1 with the measuring electrode sensors 2 in which a current is passing. The electrical connector comprises a second branch 3' electrically connecting the measuring electrode sensors 2' in which no current is passing. The electrical connector further comprises a third branch 3" electrically connecting the first and second branches 3, 3'. The third branch 3" is preferably a long and narrow electrical connector. An advantage of the arrangement of FIG. 12 is that any impedance variation of the electrical connector 3 does not alter the bio-impedance measurement. In FIG. 12 the reference electrode sensor 1 and measuring electrode sensors 2 where a current is passed are represented by the filled circles, while the measuring electrode sensors 2 where no current passes are represented by the empty circles. No current flows through the second and third electrical connectors 3', 3". Therefore, any impedance variation of the first, second and third connections 3, 3' and 3" will have no repercussions on the injected current 21 and in particular on the measured voltage u2.

Figure 13:
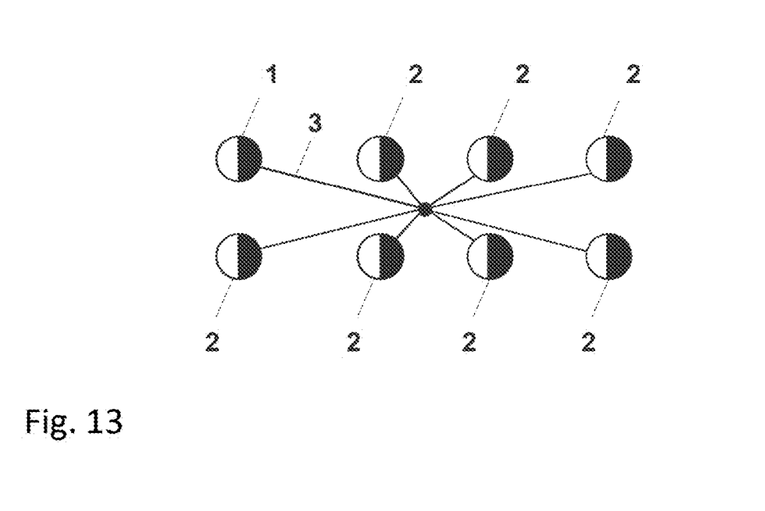
FIG. 13 illustrates an arrangement of the reference sensor electrode and measuring electrode sensors, according to another embodiment.

In the case where several current channels (each using a given frequency or time slot) are used to simultaneously measure several bioimpedance (e.g., EIT), it may be difficult to split the electrode sensors 1, 2, 2' into the two rows as illustrated in FIG. 12 since a given sensor electrode 1, 2, 2' may not be crossed by a current at a given channel and crossed at another channel. FIG. 13 illustrates a particular arrangement of the reference sensor electrode 1 and measuring electrode sensor 2 according to another embodiment. In the arrangement of FIG. 13, each of the electrode sensors 1, 2, 2' is electrically connected to a single common point (center of a star arrangement). Preferably, the area of the single point should be minimized.

Figure 14:
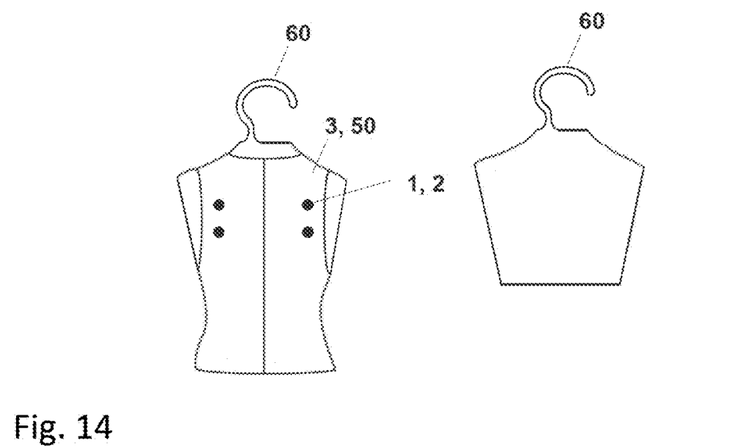
FIG. 14 shows a recharging device adapted for the measuring device, according to an embodiment.

FIG. 14 shows a method for recharging the electrode sensors 1, 2 without removing them from the garment. For example, the first electrical contact 5 of any of the electrode sensors 1, 2 can be put in electrical contact with a conductive garment support device such as a manikin or flat hanger 60. Since the electrode sensors 1, 2 are in electrical contact with each other via the electrical connector 3, the connection with the hanger 60 will allow charging the battery 43 of any one of the electrode sensors 1, 2 when a voltage is applied between the electrical connector 3 and the manikin or flat hanger 60. Short circuit between the hanger 60 and the electrical connector 3 should be avoided, for example, by using an insulation layer on the garment, or on the hanger 60 except at the location of the electrode sensors 1, 2.

Figure 15:
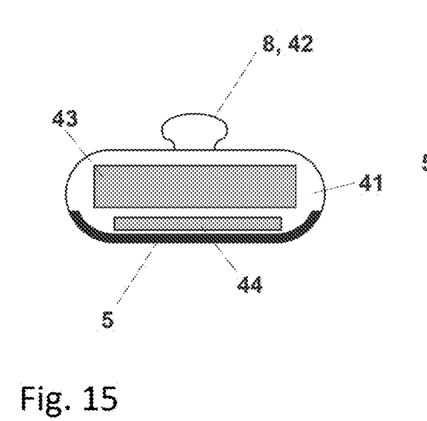
FIG. 15 represents an attachment means for attaching an electrode sensor to a garment.

FIG. 15 shows an electrode sensor 1, 2 comprising an attachment means 42, having the form of a stud button. The mechanical attachment 42 with the garment 50 also serves as electrical connector between the second electrical contact 8 and the electrical connector 3. Other attachment means can of course be used. Such attachment means can include, for instance, screw, rivet, hook-and-loop fastener (velcro), magnet, adhesive, etc.

Figure 16:
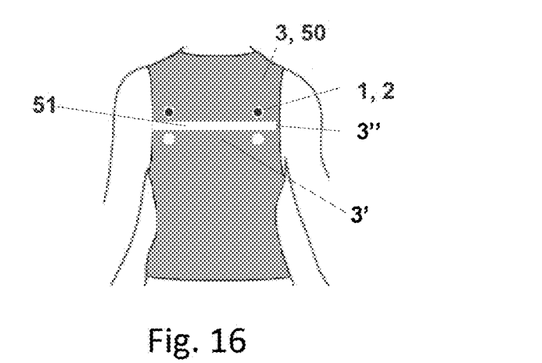
FIG. 16 illustrates an electrically conductive garment, according to an embodiment.

FIG. 16 illustrates an electrically conductive garment used as the electrical connection 3. The garment can comprises an insulating zone 51, for example made of insulated fabrics so as to have connector 3" linking the two zones 3 and 3' connecting the electrode sensors in which a current is passing and in which a current is not passing, respectively.

The invention claimed is:

1. Measurement device for measuring a bio-impedance and/or a bio-potential of a human or animal body and adapted to be worn on the body, comprising:
   at least two electrode sensors;
   each of said at least two electrode sensors comprising a first electrical contact configured to be in electrical contact with the skin of the body when the system is worn, and a second electrical contact;
   an electrical connector electrically connecting said at least two electrode sensors with each other via the second electrical contact; and
   an active device configured to provide a voltage or a current that sets the potential of the electrical connector to be equal to a calculated potential determined from the potential of the first electrical contact of each electrode sensor of a subset of said at least two electrode sensors, when the measurement device is worn.

2. The measurement device according to claim 1, wherein said at least two electrode sensors comprises a first measuring electrode sensor and a second measuring electrode sensor; and
   wherein said active device comprises a first current source included in the first measuring electrode sensor and configured to inject a first current, and another current source included in the second measuring electrode sensor and configured to inject a second current having a magnitude substantially equal to the one of the first current and opposed polarity,
   such that the potential of the electrical connector is substantially equal to a calculated potential determined from the potential of the first electrical contact of each measuring electrode sensors when the measurement device is worn; and a potential difference between the first and second measuring electrode sensors in combination with the second current can be used for measuring the bio-impedance of the body.

3. The measurement device according to claim 1, further comprising:
   at least one reference electrode sensor;
   at least two measuring electrode sensors;
   wherein said active device comprises a voltage source included in said at least one reference electrode sensor, a voltage measuring device included in at least one of the measuring electrode sensors; and
   a controller,
   wherein:
   the voltage source is controllable by the controller,
   the voltage measuring device is configured to measure a voltage between the first and second electrical contacts of said at least one of the measuring electrode sensors when the measurement device is worn; and
   the measured voltage being inputted to the controller.

4. The measurement device according to claim 3, further comprising a transmission means for transmitting the measured voltage from the voltage measuring device to an input of the controller.

5. The measurement device according to claim 4, wherein said transmission means comprises a wireless device for transmitting the voltage to the input.

6. The measurement device according to claim 4, wherein said transmission means comprises a modulator for modulating the voltage and a demodulator for demodulating the modulated voltage transmitted with a current loop, such that the modulated voltage can be inputted in the input.

7. The measurement device according to claim 6, wherein the transmission means is further configured for transmitting the measured voltage by a modulated current at a frequency above 1 kHz.

8. The measurement device according to claim 3,
wherein said at least two electrode sensors comprises one reference electrode sensor and nine measuring electrode sensors;
the voltage measuring device being included in three of the nine measuring electrode sensors and adapted for measuring a first voltage between the first and second electrical contacts for each of the three measuring electrode sensors when the measurement device is worn;
the voltage source and the voltage measuring device being configured to cooperate with the subset comprising said three of the nine measuring electrode sensors when the measured first voltage is inputted to the controller controlling the voltage source for setting the potential of the electrical connector equal to a calculated potential determined from the potential of the first electrical contact of each electrode sensor of said subset.

9. The measurement device according to claim 3, wherein the measuring electrode sensors includes a voltage measuring device configured for measuring a voltage between the first and second electrical contacts of said measuring electrode sensor when the measurement device is worn;
and wherein the voltage can be used for measuring the bio-potential of the body.

10. The measurement device according to claim 9, wherein the voltage has a sine wave with a frequency between 0 Hz and about 1000 Hz.

11. The measurement device according to claim 9,
wherein said at least two electrode sensors further comprises at least one measuring electrode sensor comprising a current source configured for injecting a impedance current; and
wherein the quotient of the voltage over the impedance current can be used for determining the bio-impedance of the body.

12. The measurement device according to claim 11, wherein the impedance current has a frequency of about 50 kHz.

13. The measurement device according to claim 3, wherein the electrical connector comprises a first branch electrically connecting said at least one reference electrode sensor with measuring sensor electrodes in which a current is passing;
a second branch electrically connecting measuring sensor electrodes in which no current is passing; and
a third branch electrically connecting the first and second branches.

14. The measurement device according to claim 3, wherein each of said at least one reference electrode sensor and measuring sensor electrodes is electrically connected to a single common point.

15. The measurement device according to claim 3 being adapted to be attached to a garment worn by the user and comprising an electrically conductive portion, such that when attached, the second electrical contacts of the electrode sensors is in electrical contact with the conductive portion of the garment;
wherein the electrical connector comprises a first branch electrically connecting said at least one reference electrode sensor with measuring sensor electrodes in which a current is passing;
a second branch electrically connecting measuring sensor electrodes in which no current is passing; and
a third branch electrically connecting the first and second branches.

16. The measurement device according to claim 3 being adapted to be attached to a garment worn by the user and comprising an electrically conductive portion, such that when attached, the second electrical contacts of the electrode sensors is in electrical contact with the conductive portion of the garment;
wherein each of said at least one reference electrode sensor and measuring sensor electrodes is electrically connected to a single common point.

17. The measurement device according to claim 1,
wherein said at least two electrode sensors comprises at least one reference electrode sensor and at least two measuring electrode sensors;
wherein said active device comprises a current source controllable by a controller and included in at least one of the measuring electrode sensors, the current source being configured for injecting a current in said at least one reference electrode sensor when the measurement device is worn;
the current source being configured to cooperate with the subset comprising said at least one reference electrode sensor when the current is inputted to the controller controlling the current source for setting the potential of the electrical connector equal to a calculated potential determined from the potential of the first electrical contact of each reference electrode sensor of said subset.

18. The measurement device according to claim 1, wherein said calculated potential comprises one of an average, a maximum, a minimum, or a median of the potential of the first electrical contact of each electrode sensor of said subset of the at least two electrode sensors.

19. The measurement device according to claim 1, being adapted to be attached to a garment worn by the user and comprising an electrically conductive portion, such that when attached, the second electrical contacts of the electrode sensors is in electrical contact with the conductive portion of the garment.

20. The measurement device according to claim 1, wherein each of electrode sensors comprises a power supply or energy harvesting device.

21. The measurement device according to claim 20 being adapted to be attached to a garment worn by the user and comprising an electrically conductive portion, such that when attached, the second electrical contacts of the electrode sensors is in electrical contact with the conductive portion of the garment;
wherein each of electrode sensors comprises a power supply or energy harvesting device; and
wherein the power supply is a battery that can be recharged when the first electrical contact of any of the electrode sensors is electrically connected to a conductive garment support device and the second electrical contact to the electrical connection.

* * * * *